United States Patent
Yee

(10) Patent No.: US 7,753,953 B1
(45) Date of Patent: Jul. 13, 2010

(54) ACCOMMODATING INTRAOCULAR LENS SYSTEM

(76) Inventor: Kingman Yee, 1913 Fumia Pl., San Jose, CA (US) 95131

( * ) Notice: Subject to any disclaimer, the term of this patent is extended or adjusted under 35 U.S.C. 154(b) by 155 days.

(21) Appl. No.: 12/079,344

(22) Filed: Mar. 26, 2008

Related U.S. Application Data

(60) Provisional application No. 60/909,068, filed on Mar. 30, 2007.

(51) Int. Cl.
*A61F 2/16* (2006.01)
(52) U.S. Cl. .................. 623/6.13; 623/6.32; 623/6.37
(58) Field of Classification Search .............. 623/6.13, 623/6.38–6.49, 6.22, 6.37
See application file for complete search history.

(56) References Cited

U.S. PATENT DOCUMENTS

| | | | |
|---|---|---|---|
| 4,373,218 A | 2/1983 | Schachar | |
| 4,601,545 A | 7/1986 | Gallivan | |
| 4,913,536 A | 4/1990 | Barnea | |
| 4,932,966 A * | 6/1990 | Christie et al. ............. | 623/6.13 |
| 5,124,734 A | 6/1992 | Barnea | |
| 5,152,788 A * | 10/1992 | Isaacson et al. ............ | 623/6.13 |
| 5,233,470 A | 12/1992 | Wu | |
| 5,684,637 A | 11/1997 | Floyd | |
| 5,731,909 A | 3/1998 | Schachar | |
| 5,774,274 A | 6/1998 | Schachar | |
| 5,864,128 A | 1/1999 | Plesko | |
| 6,038,080 A | 3/2000 | Schachar | |
| 6,188,525 B1 | 2/2001 | Silver | |
| 6,715,876 B2 | 4/2004 | Floyd | |
| 6,730,123 B1 | 5/2004 | Klopotek | |
| 7,063,723 B2 | 6/2006 | Ran | |
| 7,122,053 B2 * | 10/2006 | Esch ......................... | 623/6.13 |
| 2002/0188351 A1 * | 12/2002 | Laguette .................... | 623/6.24 |
| 2003/0060878 A1 * | 3/2003 | Shadduck ................... | 623/6.13 |
| 2005/0113911 A1 * | 5/2005 | Peyman ..................... | 623/6.11 |
| 2007/0010882 A1 * | 1/2007 | Barrett ....................... | 623/6.37 |
| 2007/0021831 A1 * | 1/2007 | Clarke ....................... | 623/6.13 |
| 2007/0088433 A1 * | 4/2007 | Esch et al. ................. | 623/6.13 |

* cited by examiner

*Primary Examiner*—Paul Prebilic
*Assistant Examiner*—Tiffany Shipmon
(74) *Attorney, Agent, or Firm*—Pinnacle Patent Law Group

(57) ABSTRACT

An accommodating intraocular lens system for implantation in a capsular bag of an eye includes an optic component comprising first and second light-transmitting lens elements that define a fluid-filled deformation chamber located between the first and second lens elements. The first and/or second lens elements have an elastic membrane adapted to deform in response to a change in pressure. The elastic membrane includes a first portion having a first deformation response and a second portion having a different second deformation response. The system also includes a refractive fluid filling the deformation chamber and at least one haptic member coupled to the optic component. The haptic member is configured for changing a hydrostatic pressure in the deformation chamber in response to muscle movement in the eye in order to deform the elastic membrane of the first and/or second lens elements, thereby changing the shape and the refractive characteristics of the optic component.

11 Claims, 6 Drawing Sheets

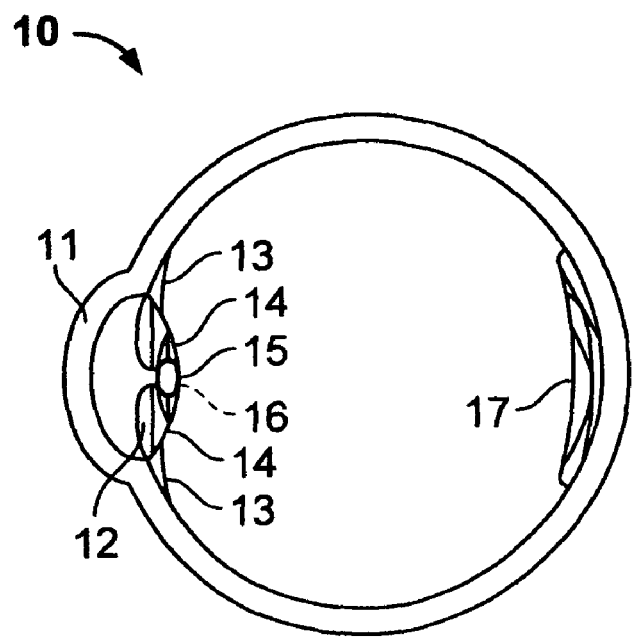
FIG. 1
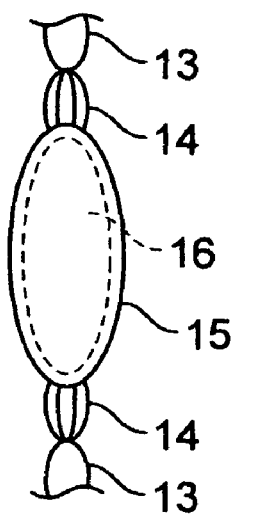 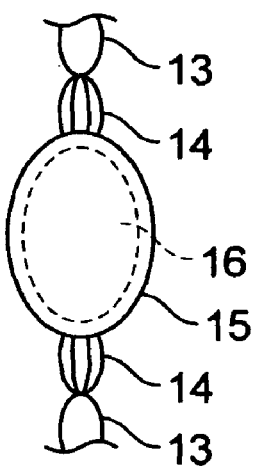
FIG. 2A  FIG. 2B

ACCOMMODATING INTRAOCULAR LENS SYSTEM

CROSS-REFERENCE TO RELATED APPLICATIONS

The application claims the benefit of priority from U.S. Provisional Application Ser. No. 60/909,068, filed Mar. 30, 2007, the disclosure of which is incorporated in its entirety by reference.

FIELD OF INVENTION

The subject matter disclosed relates to an intraocular lens system for implantation in a capsular bag of an eye. More particularly, the subject matter disclosed relates to an accommodating intraocular lens system that is responsive to the contraction and relaxation of the ciliary muscles in the eye.

BACKGROUND

As shown in FIG. 1, an eye 10 includes a cornea 11, an iris 12, ciliary muscles 13, ligament fibers or zonules 14, a capsular bag 15 that encloses a lens 16, and a retina 17. The lens 16 is composed of viscous, gelatinous transparent fibers, arranged in an "onion-like" layered structure, and is disposed in the transparent elastic capsular bag 15. The capsular bag 15 is joined by the zonules 14 around its circumference to the ciliary muscles 13, which are in turn attached to the inner surface of eye 10.

In an isolated state, the relaxed capsular bag 15 and lens 16 takes on a nearly spherical shape. When suspended within the eye 10 by the zonules 14, however, the capsular bag 15 moves between a moderately convex shape (when the ciliary muscles 13 are relaxed) to a highly convex shape (when the ciliary muscles 13 are contracted). For example, as shown in FIG. 2A, when the ciliary muscles 13 relax, the capsular bag 15 and lens 16 are pulled about the circumference, thereby flattening the lens 16 along a vertical axis. When the ciliary muscles 13 contract, the capsular bag 15 and lens 16 relax and become thicker along a horizontal axis, as shown in FIG. 2B. When the lens 16 assumes a more spherical shape, the diopter power of the lens 16 increases. Because the shape of the lens 16 can change, it is referred to as an accommodating lens in that the focal length can change to provide a sharp image at varying distances, near and far.

An intraocular lens ("IOL") is a medical device that can be implanted into the eye 10 to replace the natural lens 16. The IOL can be implanted in an intact or partial capsular bag 15. The IOL is positioned and secured in the eye 10 by one or more haptics. The IOL and haptics can be made as separate pieces attached together, or as a single integrated piece. Typical IOLs are manufactured from polymers, such as polymethylmethacrylate, polypropylene, or foldable materials such as silicone, hydrogel or acrylic.

Conventional IOLs, however, are limited. Some provide sharp vision at only one distance, that is, they have a fixed focal length or are monofocal. Other IOLs provide two or more focal distances ("multifocal lenses") and thus allow sharp vision at several distances but at the expense of contrast and sharpness as compared to a monofocal lens. For many multi-focal IOLs, only certain distances are in focus, with intermediate distances always being out of focus. Neither of these IOLs is an accommodating lens because the focal length (s) of the lens is fixed.

In some instances, accommodation can be simulated in IOLs. For example, the refractive power of an IOL can change by varying the IOL's shape, by moving the IOL along an optical axis, or by shifting several optical elements towards or away from one another. While these types of solutions can be and have been implemented in external corrective vision systems, such as spectacles or glasses, they are more challenging to implement within the eye, and particularly within the capsular bag 15.

SUMMARY

An accommodating intraocular lens system for implantation in a capsular bag of an eye is described. According to one embodiment, the system includes an optic component comprising first and second light-transmitting lens elements that define a fluid-filled deformation chamber located between the first and second lens elements. The first and/or second lens elements have an elastic membrane adapted to deform in response to a change in pressure. The elastic membrane includes a first portion having a first deformation response and a second portion having a different second deformation response. The system also includes a refractive fluid filling the deformation chamber and at least one haptic member coupled to the optic component. The haptic member is configured for changing a hydrostatic pressure in the deformation chamber in response to muscle movement in the eye in order to deform the elastic membrane of the first and/or second lens elements, thereby changing the shape and the refractive characteristics of the optic component.

BRIEF DESCRIPTION OF THE DRAWINGS

The accompanying drawings provide visual representations which will be used to more fully describe the representative embodiments disclosed here and can be used by those skilled in the art to better understand the representative embodiments and their inherent advantages. In these drawings, like reference numerals identify corresponding elements, and:

FIG. 1 is a sectional view of a human eye;

FIG. 2A and FIG. 2B are sectional side views of the lens and supporting structure of FIG. 1 showing relaxed and contracted states, respectively, of the ciliary muscles;

DETAILED DESCRIPTION

An accommodating intraocular lens ("AIOL") system that is responsive to the contraction and relaxation of the ciliary muscles in the eye is described. According to one exemplary embodiment, an AIOL system includes an optic component having at least one elastic member such that the optic component can change its shape, and therefore its refractive power, in response to the contraction and relaxation of the eye muscles during visual accommodation. In so doing, the AIOL system can selectively focus on distant and near objects.

Figure 3:
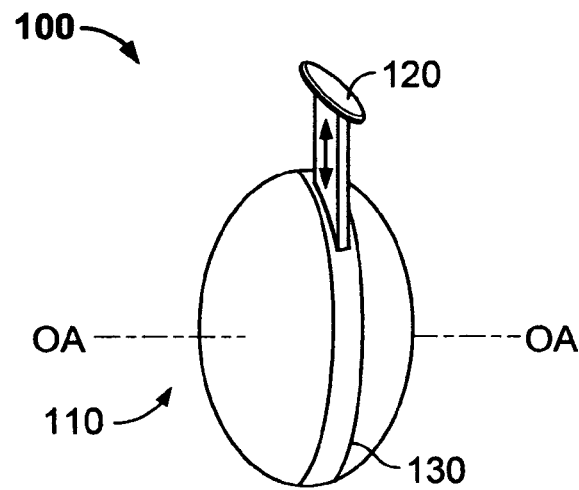
FIG. 3 is a perspective view of an exemplary lens system according to one embodiment.

In one embodiment, shown in FIG. 3, an exemplary AIOL 100 includes an optic component 110 and at least one haptic member 120 coupled to the optic component 110. The optic component 110, which has an optical axis OA, is adapted to sit within the capsular bag (not shown) and to focus light onto the retina of the eye. The haptic member 120 cooperates with the eye to effect accommodating deformation of the optic 110, and in particular increases or decreases a hydrostatic pressure in the optic component 110 to change the shape of the optic component 110.

Figure 4:
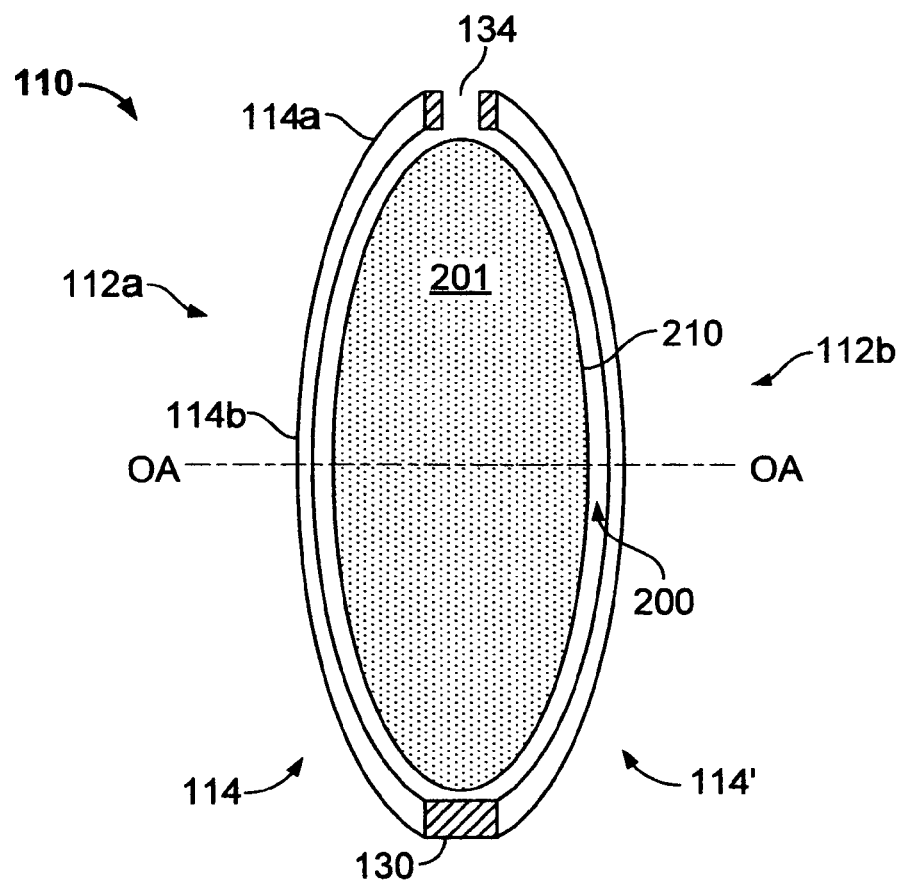
FIG. 4 is a cross-sectional view of an exemplary optic component according to one embodiment.

FIG. 4 is a cross-sectional view of the optic component 110 along an axis perpendicular to the optical axis OA according to an exemplary embodiment. The optic component 110 comprises a first light-transmitting lens element 112a and a second light-transmitting lens element 112b that define a deformation chamber 200 between the two lens elements 112a, 112b. In one embodiment, the deformation chamber 200 is filled with a refractive fluid 201. Alternatively, a light transmitting flexible bladder 210 can be used to hold with the refractive fluid 201 and the bladder 210 can be inserted into the deformation chamber 200 during implantation. As used in this description, the refractive fluid can be a liquid, as well as a gel-like substance, a gas, or a plasma. In one embodiment, the refractive indexes of the fluid 201 and first 112a and second 112b lens elements can be matching, while in another embodiment, the refractive indexes can be different.

In an exemplary embodiment, the first 112a and second 112b lens elements are disposed opposite to one another and are joined via a peripheral rim 130 that seals a periphery of the first lens element 112a to a periphery of the second lens element 112b. The peripheral rim 130 can be a separate component in one embodiment, or the peripheral rim 130 can be an extension of the periphery of the first 112a and/or second 112b lens elements in another embodiment.

In an exemplary embodiment, the first 112a and/or second 112b lens element is curved so that the curved portion(s) forms at least one convex surface. For example, in FIG. 4, the first 112a and second 112b lens elements of the optic component 110 are curved to form a double convex shape. In another embodiment, the optic component 110 can form a single convex shape when only one of the first 112a and second 112b lens elements is curved.

In one embodiment, the first 112a and/or second 112b lens elements of the optic component 110 comprises an elastic membrane 114 adapted to deform, i.e., expand or contract, in response to a change in pressure. Referring again to FIG. 3, the haptic(s) 120 is coupled to the optic component 110 at the peripheral rim 130 and positions and secures the AIOL 110 within the eye. In one embodiment, the haptic 120 is engaged with the capsular bag 15 and/or the eye's ciliary muscles 13, shown in FIG. 1, that control accommodation. When the ciliary muscles 13 contract or relax during accommodation, the muscles act on the haptic 120, causing the hydrostatic pressure of the fluid 201 in the AIOL 100 to increase or decrease. The change in pressure causes the elastic membrane 114 in the first 112a and/or second 112b lens elements to deform, i.e., expand or contract. As the curved portion or portions deform, a resultant shape of the optic component 110 forms a nearly spherical lens, an aspherical lens, or a combination of lower and higher order aberration lens. In one embodiment, the surface changes of the first 112a and second 112b lens elements are nearly spherical or parabolic in shape but with different radii of curvatures.

In one embodiment, the elastic membrane's 114 deformation response to the changes in the applied pressure within the deformation chamber 200 can vary from one portion of the elastic membrane 114 to another portion of the elastic membrane 114. In this description, the membrane's deformation response refers to an incremental expansion or contraction due to an incremental change in applied pressure, and a membrane's deformation profile refers to the deformation response spatially across the elastic membrane 114. In one embodiment, a first portion of the elastic membrane 114a can exhibit a first deformation response, while a second portion of the elastic membrane 114b can exhibit a second deformation response that differs from the first deformation response. By varying and controlling the deformation response of the elastic membrane 114 in different portions, the resultant shape of the optic component 110 can be controlled to produce a customized lens for an individual.

Figure 5A:
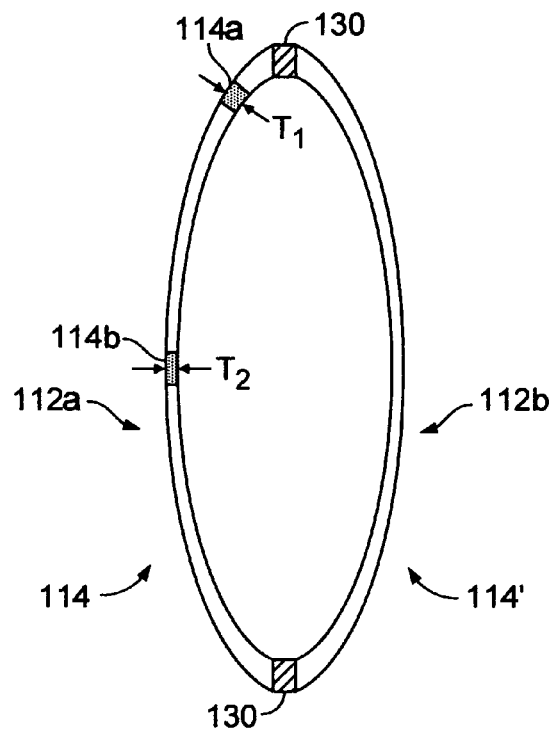
FIG. 5A is a cross-sectional view of an exemplary optic component according to another embodiment.

In one embodiment, the deformation response of the elastic membrane 114 can be varied by the membrane's spatial thickness profile. FIG. 5A is a cross-section view of an optic component 110 according to one embodiment where a first portion of the elastic membrane 114a has a first thickness, $T_1$, and a second portion of the elastic membrane 114b has a second thickness, $T_2$ different from the first thickness. Because the deformation response is dependent on the thickness of the elastic membrane 114, the first portion 114a will exhibit a first deformation response and the second portion 114b will exhibit a second deformation response different from the first deformation response. Moreover, the difference between the first and second deformation responses will be based on the difference between the first and second thicknesses of the first 114a and second 114b portions, respectively.

Figure 5B:
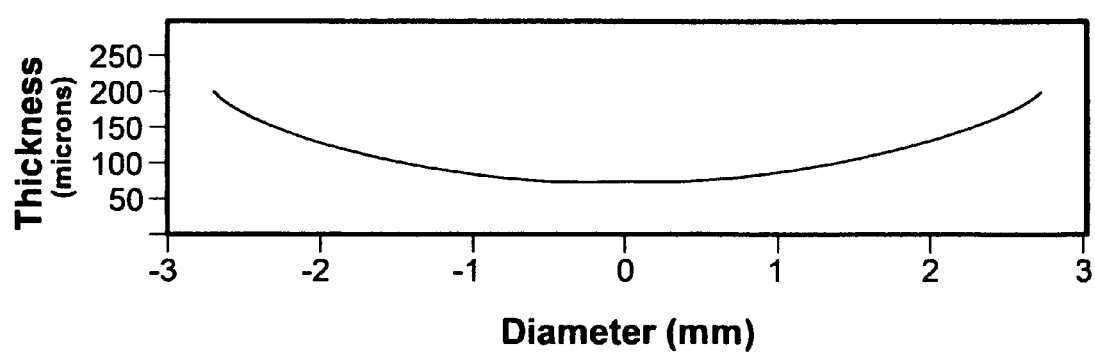
FIGS. 5B-5D are exemplary graphical representations of a thickness profile, deformation response and variable deformation response, respectively, of the optic component depicted in FIG. 5A according to one embodiment.
Figure 5C:
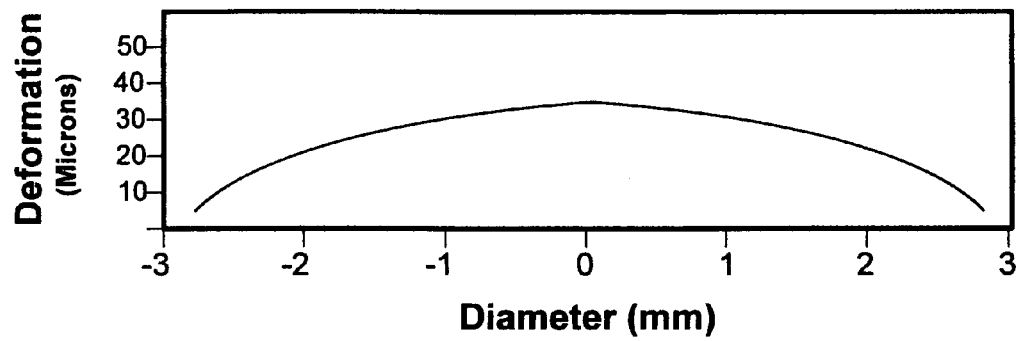
Figure 5D:
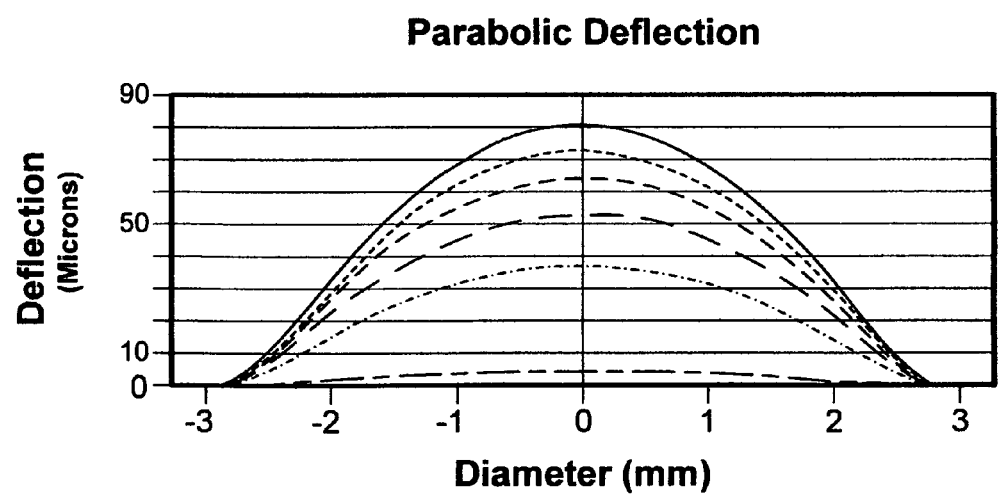

For example, FIG. 5B is a thickness profile of an elastic membrane 114 that indicates that the membrane 114 is thicker at the first portion 114a (near the periphery) and thinner at the second portion 114b (near the optical axis) and FIG. 5C is a deformation profile at a given applied pressure of the elastic membrane 114 having a thickness profile similar to that shown in FIG. 5B. Because the deformation response of the elastic membrane 114 is inversely proportional to the thickness of the elastic membrane 114, the elastic membrane 114 can stretch more at the second portion 114b (near the center) than at the first portion 114a (near the periphery), resulting in a cone shaped lens. FIG. 5D is a graph showing a simulation of the resultant shape of the lens when subjected to a plurality of applied pressures for the elastic membrane 114 having a thickness profile similar to that shown in FIG. 5B. As the applied pressure increases, the lens becomes more cone shaped due to the variable thickness profile.

According to an exemplary embodiment, the deformation response of the elastic membrane 114 and thereby the resultant shape of the optic component 110 can be controlled by controlling the thickness profile of the elastic membrane 114. For example, a larger difference of thickness between the first 114a and second 114b portions can result in a more cone shaped lens at lower pressures. In another example, a thickness profile that is thick at the periphery, thinner between the periphery and the center, and thicker at the center can produce a lens with bulging sides and a relatively flat central zone. Accordingly, a lens designer can have great flexibility in controlling the resultant shape of the optic component 110 to produce a customized lens for an individual.

In another embodiment, the deformation response of the elastic membrane 114 can be varied by changing its material properties, in particular the elasticity, of different portions of the elastic membrane 114. In this embodiment, the first portion of the elastic membrane 114a can have a first elasticity and the second portion of the elastic membrane 114b can have a second elasticity different from the first elasticity. Because the deformation response is dependent on the elasticity of the elastic membrane 114, the first portion 114a will exhibit a first deformation response and the second portion 114b will exhibit a second deformation response different from the first deformation response. Moreover, the difference between the first and second deformation responses will be based on the difference between the first and second elasticities of the first 114a and second 114b portions, respectively.

In one embodiment, the elasticity of the elastic membrane 114 can be changed locally by altering the physical properties of the material affecting its elasticity. For example, the elasticity of a portion of the elastic membrane 114a can be changed locally by doping the first portion 114a with another material at a first concentration and/or doping the second portion 114b with the same or a different dopant at the same, or a second, concentration. Alternatively or in addition, the elasticity of a portion of the elastic membrane 114 can be modified by applying a spot heat treatment, or by applying any other process that changes the elastic characteristics of the elastic membrane 114. For example, the first portion of the elastic membrane 114a can be exposed to a laser beam with a spatial energy profile that induces differential polymerization at the first portion 114a thereby changing the elasticity of the elastic membrane at the first portion 114a. In one embodiment, selectively varying the elasticity of the elastic membrane 114 can result in substantially similar deformation characteristics as those shown in FIG. 5C and FIG. 5D.

Referring again to FIG. 5A, the first lens element 112a can have a first elastic membrane 114 that exhibits a first deformation profile and the second lens element 112b can have a second elastic membrane 114' that exhibits a second deformation profile. For example, the first elastic membrane 114 can have a first thickness profile and the second elastic membrane 114' can have a second thickness profile. In this embodiment, when the applied pressure in the deformation chamber 200 changes, the first 114 and second 114' elastic membranes respond differently to the same applied pressure based on the first and second deformation profiles, respectively, such that the shape of the optic component 110 can be asymmetrical along an axis perpendicular to the optical axis. For example, the resulting radius of curvature of the first lens element 112a can be different from the resulting radius of curvature of the second lens element 112b. Accordingly, the resultant shape of the optic component 110 can be customized according to the respective deformation profiles of the first 114 and second 114' elastic membranes.

In one embodiment, the hydrostatic pressure within the deformation chamber 200 can be increased or decreased by a fluid piston pump well known to those with ordinary skill in the art. In another embodiment, a change in applied pressure can be achieved via a portion of the haptic member 120 pressing against the peripheral rim 130 or against the fluid filled bladder 210 within the deformation chamber 200. When the portion of the haptic member 120 presses against the peripheral rim 130 or against the fluid filled bladder 210, the volume of the deformation chamber 200 necessarily decreases, which in turn increases the hydrostatic pressure within the chamber 200.

Referring again to FIG. 4, the peripheral rim 130 can include an attachment component (not shown) and a slot 134 extending through the peripheral rim 130 and into the deformation chamber 200 according to an exemplary embodiment. The attachment component is configured for coupling the haptic member 120 to the optic component 110 and the slot 134 is adapted to allow a portion of the haptic member 120 to move into and out of the deformation chamber 200 in response to the contraction and relaxation, respectively, of the ciliary muscle of the eye during accommodation.

Figures 6A, 6B, 6C:
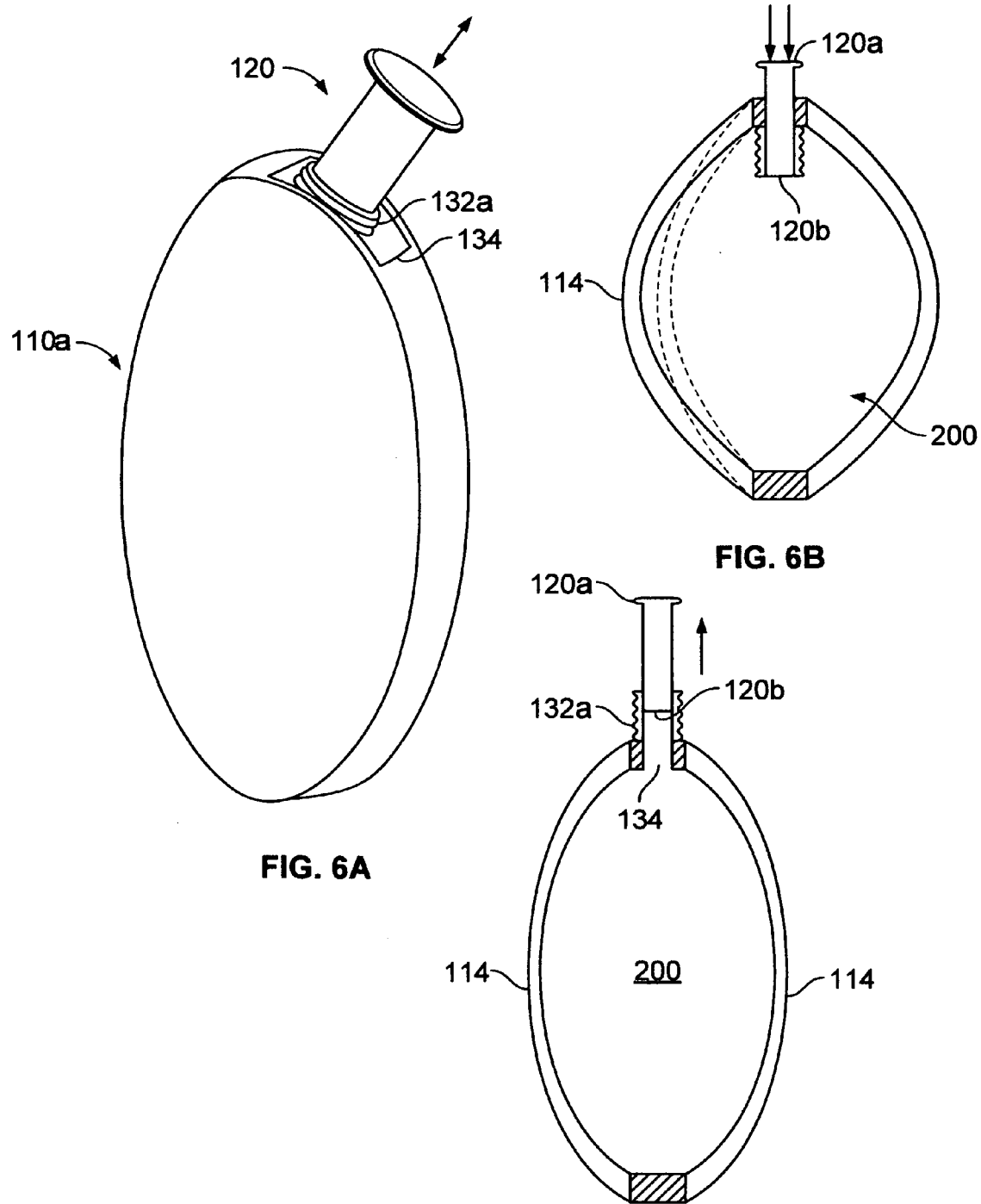
FIGS. 6A-6C are perspective and cross-sectional views respectively of an exemplary lens system according to one exemplary embodiment.

For example, in one embodiment shown in FIGS. 6A-6C, the attachment component can comprise a pleated accordion component 132a that is integrated with the slot 134. The haptic member 120 includes an outer portion 120a adapted to engage an inner surface of the capsular bag (not shown). In one embodiment, the outer portion 120a can be attached to the ciliary muscle and/or the inner surface of the capsular bag (not shown). The haptic member 120 also has an inner portion 120b disposed opposite to the outer portion 120a and connected to the pleated accordion component 132a. In this embodiment, the pleated accordion component 132a allows the inner portion 120b of the haptic member to slidably fit in the slot 134 and to slide toward and away from the center of the optic component 110a.

When the ciliary muscles of the eye contract during accommodation, the inner surface of the capsular bag contracts and pushes the outer portion 120a of the haptic member which causes the inner portion 120b to slide into the deformation chamber 200 via the slot 134 toward the center of the optic component 110. Such movement increases the hydrostatic pressure within the deformation chamber 200, which causes the elastic membrane(s) 114 to deform outward thereby making the lens element 112 more convex, as shown in FIG. 6B. When the ciliary muscle relaxes, the inner surface of the capsular bag expands and releases and/or pulls the outer portion 120a of the haptic member so that the inner portion 120b slides away from the center of the optic component 110a. Such movement decreases the hydrostatic pressure within the deformation chamber 200, which causes the elastic membrane(s) 114 to return to its unstressed state thereby making the lens element 112 less convex, as shown in FIG. 6C. Thus, as the eye focuses on objects at varying distances, the pleated accordion component 132a allows the haptic member 120 to move toward or away from the center of the optic component 110a, which causes the hydrostatic pressure to change within the deformation chamber 200.

Figure 7:
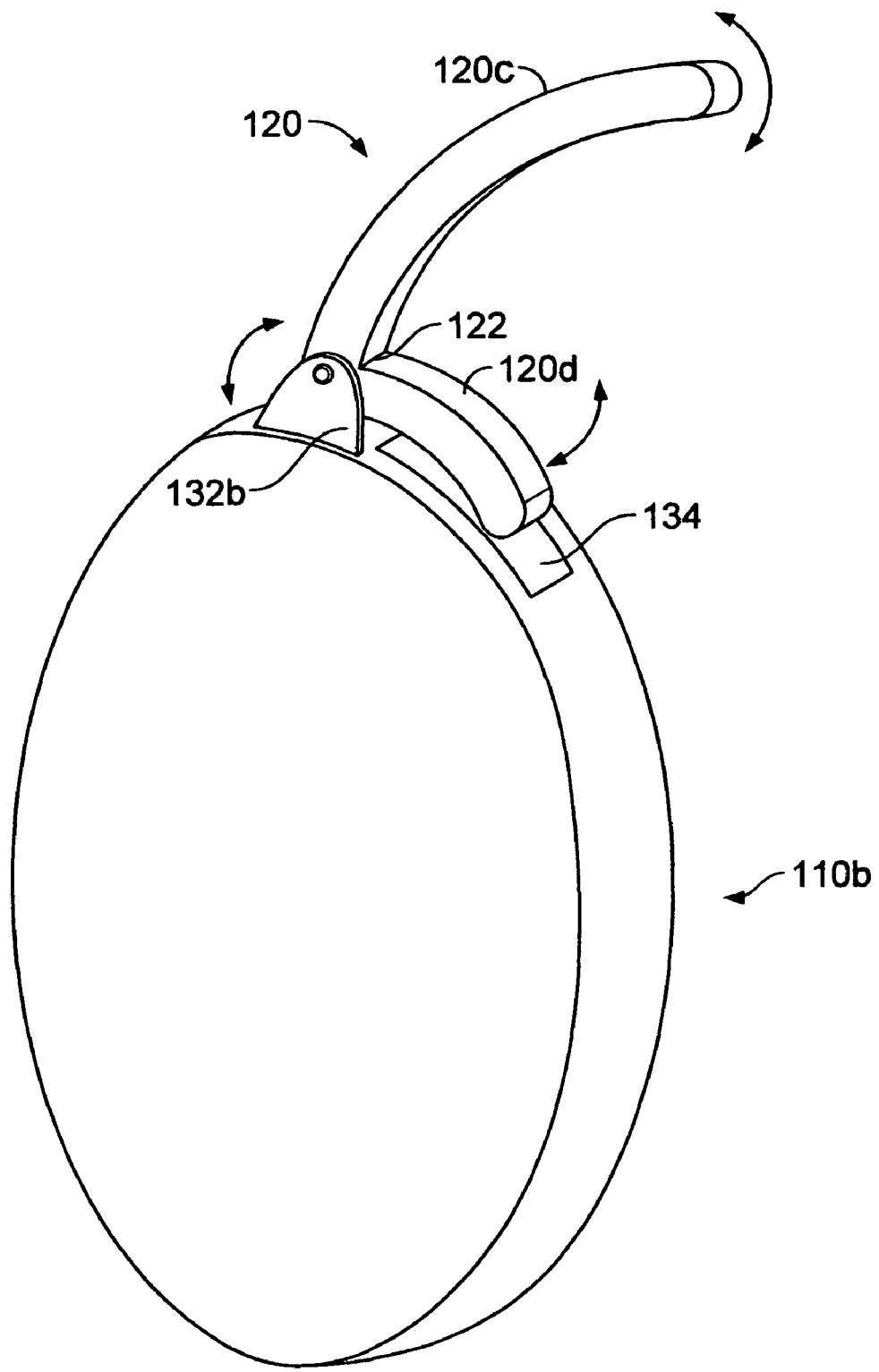
FIG. 7 is a perspective view of another exemplary lens system according to another exemplary embodiment.

In another embodiment, shown in FIG. 7, the haptic member 120 can comprise an accommodation arm 120c rigidly connected to a displacement arm 120d at an elbow 122 forming an acute angle between the accommodation 120c and displacement 120d arms. In this embodiment, the accommodation arm 120c is engaged with and/or attached to the ciliary muscle and/or the inner surface of the capsular bag (not shown). The attachment component comprises a hinge component 132b that pivotally couples the haptic member 120 at the elbow 122 and positions the displacement arm 120d at the slot 134 such that the displacement arm 120d can rotate into and out of the deformation chamber 200 via the slot 134.

When the ciliary muscle of the eye contracts during accommodation, the inner surface of the capsular bag contracts and pushes the accommodation arm 120c in a manner causing it to rotate about the hinge component 132b which causes the displacement arm 120d to rotate into the deformation chamber 200 via the slot 134. Such movement increases the hydrostatic pressure within the deformation chamber 200, which causes the elastic membrane(s) 114 to deform outwardly thereby making the lens element 112 more convex. Conversely, when the ciliary muscle relaxes, the inner surface of the capsular bag expands and releases or pulls the accommodation arm 120c so that the displacement arm 120d rotates out of the deformation chamber 200. Such movement decreases the hydrostatic pressure within the deformation chamber 200, which causes the elastic membrane(s) 114 to return to its unstressed state thereby making the lens element 112 less convex.

According to exemplary embodiments, an accommodating intraocular lens system includes an optic component 110 having at least one flexible elastic membrane 114 adapted to deform in response to a change in pressure within the optic component 110. The elastic membrane 114 has a first portion 114a that exhibits a first deformation response and a second portion 114b that exhibits a second deformation response that differs from the first deformation response. Accordingly, because the elastic membrane 114 can have varying deformation responses in different portions, it can form deformation profiles that are nearly spherical, parabolic, aspherical, or a combination of lower and higher order Zernikes.

It will be appreciated by those of ordinary skill in the art that the concepts and techniques described here can be embodied in various specific forms without departing from the essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

What is claimed is:

1. An accommodating intraocular lens system for implantation in a capsular bag of an eye, the system comprising:
   an optic component comprising a first light-transmitting lens element and a second light-transmitting lens element defining a fluid-filled deformation chamber located between the first and second lens elements, at least one of the first and second lens elements comprising an elastic membrane adapted to deform in response to a change in pressure, the elastic membrane including a first portion having a first deformation response and including a second portion having a second deformation response, wherein the first deformation response differs from the second deformation response, and comprising a peripheral rim sealing a periphery of the first lens element to a periphery of the second lens element;
   a refractive fluid filling the deformation chamber; and
   at least one haptic member coupled to the optic component and configured for changing a hydrostatic pressure in the deformation chamber in response to muscle movement in the eye in order to deform the elastic membrane of at least one of the first and second lens elements, thereby changing the shape and the refractive characteristics of the optic component,
   wherein the peripheral rim including an attachment component for coupling the at least one haptic member to the optic component and a slot extending into the deformation chamber for allowing a portion of the at least one haptic member to move into and out of the deformation chamber in response to a contraction and a relaxation of the eye during accommodation, wherein the at least one haptic member comprises an accommodation arm adapted to engage an inner surface of the capsular bag and a displacement arm, the accommodation arm rigidly connected to the displacement arm at an elbow and forming an acute angle with the displacement arm, and wherein the attachment component comprises a hinge portion that pivotally couples the at least one haptic member at the elbow and positions the displacement arm at the slot such that when the capsular bag contracts and relaxes during accommodation, the displacement arm rotates into and out of the deformation chamber via the slot, thereby changing the hydrostatic pressure therein.

2. The system of claim 1 wherein the first portion of the elastic membrane has a first thickness and the second portion of the elastic membrane has a second thickness and wherein the difference between the first and second deformation responses is based on a difference between the first and second thicknesses of the first and second portions, respectively.

3. The system of claim 2 wherein the first portion is located at a periphery of the elastic membrane and the second portion is located approximately near a center of the elastic membrane and wherein the first thickness is greater than the second thickness such that the deformation response near the center of the elastic membrane is greater than the deformation response at the periphery.

4. The system of claim 2 wherein a thickness of the elastic membrane varies such that when the hydrostatic pressure in the deformation chamber changes, a resulting shape of the optic component can be controlled based on the varying thickness of the elastic membrane.

5. The system of claim 1 wherein the first portion of the elastic membrane has a first elasticity and the second portion of the elastic membrane has a second elasticity and wherein the difference between the first and second deformation responses is based on a difference between the first and second elasticities of the first and second portions, respectively.

6. The system of claim 5 wherein an elasticity of the elastic membrane varies such that when the hydrostatic pressure in the deformation chamber changes, a resulting shape of the optic component can be controlled based on the varying elasticity of the elastic membrane.

7. The system of claim 5 wherein the first portion of the elastic membrane is exposed to a laser beam with a spatial energy profile that induces differential polymerization at the first portion thereby changing the elasticity of the elastic membrane at the first portion.

8. The system of claim 5 wherein the first portion of the elastic membrane is doped with another material thereby changing the elasticity of the elastic membrane at the first portion.

9. The system of claim 1 wherein the first lens element comprises a first elastic membrane having a first deformation profile and the second lens element comprises a second elastic membrane having a second deformation profile such that when the hydrostatic pressure in the deformation chamber is changed, each of the first and second elastic membranes is displaced based on the first and second deformation profiles, respectively.

10. The system of claim 9 wherein the first deformation profile is different from the second deformation profile such that the shape of the optic component is asymmetrical.

11. The system of claim 1 further comprising a light transmitting flexible bladder for holding the refractive fluid.

* * * * *